United States Patent
Schaus

(10) Patent No.: US 8,420,654 B2
(45) Date of Patent: Apr. 16, 2013

(54) 1,5-DIPHENYL-PYRROLIDIN-2-ONE COMPOUNDS AS CB-1 LIGANDS

(75) Inventor: John Mehnert Schaus, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 250 days.

(21) Appl. No.: 12/935,596

(22) PCT Filed: Apr. 2, 2009

(86) PCT No.: PCT/US2009/039293
§ 371 (c)(1),
(2), (4) Date: Sep. 30, 2010

(87) PCT Pub. No.: WO2009/131815
PCT Pub. Date: Oct. 29, 2009

(65) Prior Publication Data
US 2011/0034484 A1    Feb. 10, 2011

Related U.S. Application Data

(60) Provisional application No. 61/046,943, filed on Apr. 22, 2008.

(51) Int. Cl.
*C07D 403/12* (2006.01)
*A61K 31/506* (2006.01)

(52) U.S. Cl.
USPC .......................................... 514/256; 544/335

(58) Field of Classification Search ................. 544/335; 514/256
See application file for complete search history.

(56) References Cited

FOREIGN PATENT DOCUMENTS

| WO | 2005/077911 A | 8/2005 |
|----|---------------|--------|
| WO | 2005080345 A | 9/2005 |
| WO | 2007/020502 A | 2/2007 |
| WO | 2008/070305 A | 6/2008 |
| WO | 2008/070306 A | 6/2008 |

OTHER PUBLICATIONS

Jang et al., Pharmacokinetics and Its Role in Small Molecule Drug Discovery Research, Medicinal Research Reviews, vol. 21, No. 5, pp. 382-396, 2001.
Delapp et al, Determination of [35S]Guanosine-5'-O-(3-thio)Triphosphate Binding mediated by Cholinergic Muscarinic Receptors in Membranes from Chinese Hamster Ovary Cells and Rat Striatum Using an Anti-G Protein Scintillation Proximity Assay1, The Journal of Pharmacology and Experimental Therapeutics, vol. 289, No. 2, pp. 946-955, 1999.
Cheng et al., Relationship Between the Inhibition Constant (KI) and the Concentration of Inhibitor Which Causes 50 Percent Inhibition (I50) of an Enzymatic Reaction, Biochemical Pharmacology, vol. 22, pp. 3099-3108 1973.
Andreichikov et al., Zhurnal Organicheskoi Khimii, vol. 22, No. 10, pp. 2208-2203 1986.
Pacher et al., The Endocannabinoid System as an Emerging Target of Pharmacotherapy, vol. 58, No. 3, pp. 389-462, 2006.

*Primary Examiner* — Deepak Rao
(74) *Attorney, Agent, or Firm* — R. Craig Tucker

(57) ABSTRACT

CB-1 receptor inverse agonist compounds of Formula

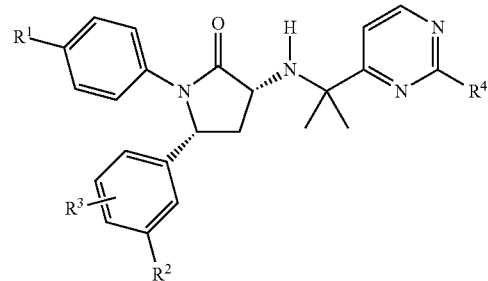

and pharmaceutical compositions for the treatment of obesity or cognitive impairment associated with schizophrenia.

13 Claims, No Drawings

1,5-DIPHENYL-PYRROLIDIN-2-ONE COMPOUNDS AS CB-1 LIGANDS

This application is a United States national phase entry, pursuant to 35 U.S.C. 371, of PCT/US2009/039293, filed Apr. 2, 2009, which claims the benefit of U.S. provisional patent application No. 61/046,943, filed Apr. 22, 2008

The cannabinoid CB-1 receptor (CB-1) is primarily found in the central and peripheral nervous systems and to a lesser extent in several peripheral organs. The cannabinoid CB-2 receptor (CB-2) is found primarily in the immune system. The pharmacology and therapeutic potential for cannabinoid receptor ligands has been reviewed (Pacher, et al. Pharmacol. Rev. (2006) 58, 389)). CB-1 receptor antagonists/inverse agonists have been shown effective for reducing feeding and body weight in animal models of obesity. CB-1 antagonists/inverse agonists have been shown to further potentiate the activity of antipsychotic agents in various assays and may be effective in treating both negative and cognitive symptoms of schizophrenia. In addition, the weight loss effects of CB-1 antagonists/inverse agonists have been demonstrated in animal models of antipsychotic treatment-induced weight gain and therefore may also be effective in controlling the treatment-emergent weight gain and metabolic syndrome seen with current antipsychotic therapies. Moreover, CB-1 receptor antagonists/inverse agonists have been shown to reduce alcohol consumption in animal models of alcohol drinking and therefore may be useful in the treatment of alcoholism and/or substance abuse.

Compounds acting at the CB-2 receptor may have effects on immune function. Therefore, in developing therapeutic agents active at the CB-1 receptor, it is desirable to have high selectivity for the CB-1 receptor versus the CB-2 receptor to avoid undesirable effects.

A number of centrally acting CB-1 receptor antagonists/inverse agonists have been studied for the treatment of obesity and/or other disorders. As for example, WO2007/020502 discloses certain substituted pyrrolidin-2-one compounds as CB-1 antagonists.

Oral administration is typically the preferred route of administration for agents for the treatment of obesity and/or schizophrenia. For compounds to display good oral bioavailability, they typically must have good aqueous solubility and sufficient metabolic stability to minimize first pass degradation in the liver. Endogenous cannabinoid ligands and the complementary site to which they bind in the CB-1 receptor are highly lipophilic. Consequently, known CB-1 receptor ligands have also tended to be lipophilic, which leads to poor solubility. Also many CB-1 receptor ligands have been relatively metabolically labile. These solubility and/or metabolism properties of many CB-1 compounds have resulted in limited oral absorption and bioavailability.

Oxidative metabolism of some compounds may lead to the formation of reactive, electrophilic metabolic intermediates. Such intermediates are prone to reaction with other nucleophiles in the body such as proteins, glutathione, DNA, RNA, etc., which can lead to undesirable toxic effects.

The pharmacokinetic properties of a therapeutic agent can be influenced by the co-administration of other agents. These so-called drug-drug interactions may lead to either an increase or decrease in the plasma exposure of the therapeutic agent, leading to problems with tolerability and/or efficacy of the agent. Compounds which are metabolically cleared through saturatable mechanisms, (e.g. CYP3A4, CYP2D6, CYP2C9, and CYP1A2) are particularly prone to suffer from such drug-drug interactions. Conversely, compounds that inhibit these saturatable mechanisms are prone to cause such drug-drug interactions. Some known CB-1 antagonists/inverse agonists exhibit such liabilities.

There remains a need for CB-1 receptor antagonists or inverse agonists that have high selectivity over CB-2 receptor, have high in vivo potency (low nM $K_b$), have acceptable bioavailability, that do not form reactive metabolic intermediates, and that have decreased potential for drug-drug interactions. The compounds of the present invention provide some or all of these advantages.

The present invention provides compounds of Formula (I)

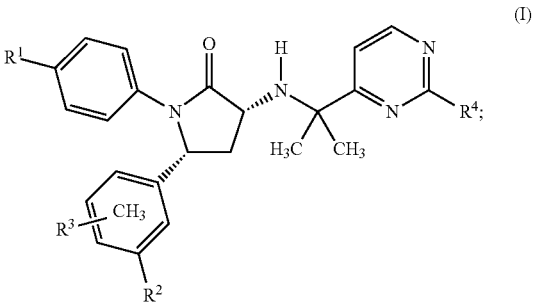

Wherein:

$R^1$ is selected from the group consisting of hydrogen, chloro, cyano, trifluoromethyl, difluoromethoxy, and trifluoromethoxy;

$R^2$ is selected from the group consisting of hydrogen, halo, cyano, $(C_1$-$C_3)$ alkyl substituted with from 1 to 5 fluoro groups, and $(C_1$-$C_3)$ alkoxy substituted with from 1 to 5 fluoro groups;

$R^3$ is selected from the group consisting of hydrogen, fluoro, and chloro;

$R^4$ is selected from the group consisting of trifluoromethyl, cyano and cyclopropyl;

provided that, when $R^1$ is hydrogen, chloro, cyano, or trifluoromethyl, then $R^2$ is $(C_1$-$C_3)$ alkoxy substituted with from 1 to 5 fluoro groups;

and pharmaceutically acceptable salts thereof.

One of ordinary skill in the art will recognize that the compounds of the present invention may exist in forms having different points of attachment of particular hydrogen atoms and are thus tautomeric. The individual tautomers as well as mixtures thereof are contemplated within the scope of the compounds of Formula (I) as if specifically drawn. Each of the forms of the tautomer may exist, interconvert, and undergo the tautomerization under the conditions specified.

Another aspect of the present invention provides a pharmaceutical composition comprising a compound according to Formula (I), or a pharmaceutically acceptable salt thereof, and a pharmaceutically acceptable carrier, diluent, or excipient.

One embodiment of this aspect of the invention provides a pharmaceutical composition comprising a compound according to Formula (I), or a pharmaceutically acceptable salt thereof, and a pharmaceutically acceptable carrier, diluent, or excipient, wherein the optical purity of the single stereoisomer of the compound of Formula (I) or salt thereof is greater than 90%, preferably greater than 95%, as for example, greater than 99%.

Another aspect of the present invention provides a compound according to Formula (I), or a pharmaceutically acceptable salt thereof, for use in therapy.

One embodiment of this aspect of the present invention provides a compound according to Formula (I), or a pharmaceutically acceptable salt thereof, for use in the treatment of an eating disorder associated with excessive food intake, weight gain, obesity, schizophrenia, cognitive impairment associated with schizophrenia, negative symptoms associated with schizophrenia, substance abuse, alcohol dependence, and/or weight gain associated with treatment with an antipsychotic, or as an aid for smoking cessation.

Another embodiment of this aspect of the invention provides a compound according to Formula (I), or a pharmaceutically acceptable salt thereof, for use in simultaneous, separate, or sequential combination treatment with an antipsychotic agent in a treatment for weight gain, obesity, schizophrenia, cognitive impairment associated with schizophrenia, negative symptoms associated with schizophrenia, and/or weight gain associated with treatment with an antipsychotic.

In another aspect of the present invention, there is provided the use of a compound according to Formula (I), or a pharmaceutically acceptable salt thereof, in the manufacture of a medicament for the treatment of an eating disorder associated with excessive food intake, weight gain, obesity, schizophrenia, cognitive impairment associated with schizophrenia, negative symptoms associated with schizophrenia, substance abuse, alcohol dependence, and/or weight gain associated with treatment with an antipsychotic, or for an aid for smoking cessation.

One embodiment of this aspect of the invention provides the use of a compound according to Formula (I), or a pharmaceutically acceptable salt thereof, in the manufacture of a medicament for use in combination therapy for weight gain, obesity, schizophrenia, cognitive impairment associated with schizophrenia, negative symptoms associated with schizophrenia, and/or weight gain associated with treatment with an antipsychotic, wherein said medicament is to be administered in simultaneous, separate or sequential combination with an antipsychotic.

In another aspect of this aspect of the invention there is provided a method for the treatment of an eating disorder associated with excessive food intake, weight gain, obesity, schizophrenia, cognitive impairment associated with schizophrenia, negative symptoms associated with schizophrenia, substance abuse, alcohol dependence, and/or weight gain associated with treatment with an antipsychotic, or for an aid for smoking cessation in a mammal, particularly a human, comprising administering to a mammal in need of such treatment, an effective amount of a compound according to Formula (I) or a pharmaceutically acceptable salt thereof.

Another embodiment of this aspect of the invention provides a method for the treatment of weight gain, obesity, schizophrenia, cognitive impairment associated with schizophrenia, negative symptoms associated with schizophrenia, and/or weight gain associated with treatment with an antipsychotic in a human, comprising administering to a human in need of such treatment, an effective amount of a compound according to Formula (I), or a pharmaceutically acceptable salt thereof, in simultaneous, separate, or sequential combination with an antipsychotic.

Additionally, the present invention provides a pharmaceutical formulation adapted for the treatment of an eating disorder associated with excessive food intake, weight gain, obesity, schizophrenia, cognitive impairment associated with schizophrenia, negative symptoms associated with schizophrenia, substance abuse, alcohol dependence, and/or weight gain associated with treatment with an antipsychotic, or for an aid for smoking cessation, comprising a compound of Formula (I), or a pharmaceutically acceptable salt thereof, in association with a pharmaceutically acceptable carrier, diluent or excipient.

In the use of the compounds of the present invention in the simultaneous, separate, or sequential combination treatment with an antipsychotic, an atypical antipsychotic is preferred, as for example olanzapine, clozapine, and/or risperidone.

Compounds of Formula (I) are selective inverse agonists or antagonists for the CB-1 receptor. The compounds are particularly selective for the CB-1 receptor over the CB-2 receptor. As inverse agonists (or antagonists) of the CB-1 receptor, the compounds are useful for treatment and/or prevention of conditions associated with the CB-1 receptor. Such conditions include, for example, eating disorders associated with excessive food intake, obesity, schizophrenia, particularly the negative symptoms associated with schizophrenia, as for example cognitive impairment associated with schizophrenia, substance abuse, alcohol dependence, smoking cessation and weight gain associated with treatment with an antipsychotic. See DSM-IV-TR., *Diagnostic and Statistical Manual of Mental Disorders. Revised,* $4^{th}$ Ed., Text Revision (2000). The skilled artisan will recognize that there are alternative nomenclatures, nosologies, and classification systems for pathologic psychological conditions and that these systems evolve with medical scientific progress.

The compounds of Formula (I) can also be used to ameliorate weight gain, whether or not the associated weight gain subject can be classified as clinically obese.

Another aspect of the present invention provides a cosmetic method of inducing weight loss comprising administering to a human a compound of formula (I).

An effective amount of the compounds of Formula (I) may be administered to a patient in need of such treatment or prophylaxis in order to practice the present methods of therapy. The need for a prophylactic administration according to the methods of the present invention is determined via the use of well-known risk factors. The effective amount of an individual compound is determined, in the final analysis, by the physician in charge of the treatment, but depends on factors such as the disorder to be treated, the severity of the disorder and other diseases or conditions present, the chosen route of administration, other drugs and treatments which the patient may concomitantly require, and other factors in the physician's judgment. The magnitude of therapeutic or prophylactic dose of a compound of Formula (I) will, of course, vary with the patient size and age, the nature and severity of the condition to be treated, the particular compound used, and the desired route of administration.

The dose may be administered in a single daily dose or the total daily dosage may be administered in divided multiple doses, as for example two, three, or four times daily. Furthermore, based on the properties of the individual compound selected for administration and/or the characteristics of the dosage form (i.e., modified release), the dose may be administered less frequently, e.g., weekly, twice weekly, monthly, etc. The unit dosage may be correspondingly larger for the less frequent administration. When administered via, transdermal routes, or through a continual intravenous solution, the dosage administration will, of course, be continuous rather than intermittent throughout the dosage regimen.

As used above and throughout the description of the invention, the following terms, unless otherwise indicated, will have the following meaning:

As used herein the term "$(C_1-C_3)$alkyl" refers to methyl, ethyl, propyl, and isopropyl.

"Halo" refers to a fluoro, chloro, or bromo.

"$(C_1-C_3)$alkoxy" refers to methoxy, ethoxy, propoxy, and isopropoxy.

"Inverse agonist(s)" shall refer to those compounds which possess negative intrinsic activity by reversing the constitutive activity of the receptor. Inverse agonists act to inhibit or reverse the activity of agonists.

"Obesity" refers to the condition of having a high amount of body fat. A person is considered obese if he or she has a body mass index (BMI) of 30 kg/m² or greater. A person with BMI=27-30 is generally considered overweight. Conventionally, those persons with normal weight have a BMI of 19.9 to 26.9. The obesity may be due to any cause, whether genetic or environmental. Examples of disorders that may result in obesity or be the cause of obesity include overeating, decreased physical activity and pathological conditions showing reduced metabolic activity. The invention is not affected by the exact definition of obesity by the BMI standard and all such definitions are to be considered as equivalents.

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula (I)). It is understood by those of ordinary skill in this art that the terms "pharmaceutical formulation" and "pharmaceutical composition" are generally interchangeable, and they are so used for the purposes of this application. It will also be understood that a pharmaceutical composition according to the present invention will have one or more compounds of Formula (I) and may also contain one or more other active ingredients as desired for a given pharmaceutical composition.

"Prevention" (of obesity or weight gain) refers to preventing obesity from occurring if the treatment is administered prior to the onset of the obese condition. Moreover, if treatment is commenced in an already obese subject, such treatment is expected to prevent, or to prevent the progression of further weight gain. One example of such prevention is to prevent further weight gain in a human undergoing treatment with an antipsychotic.

Abbreviations used herein are defined as follows:
"THF" means tetrahydrofuran.
"MTBE" means methyl tert-butyl ether.
"HOAc" means acetic acid.
"Et$_2$O" means diethyl ether.
"BSA" means bovine serum albumin.
"GDP" means guanosine diphosphate.
"GTP" means Guanosine-5'-triphosphate.
"GTP-γ$^{35}$S" means Guanosine-5' (γ-thio)-triphosphate.
"HEPES" means (4-(2-hydroxyethyl)-1-piperazineethanesulfonic acid).
"HOAc" means acetic acid.
"i.v" or "iv" means intravenous.
"p.o." or "po" means orally.
"THF" means tetrahydrofuran.
"T$_r$" means retention time.

While all of the compounds of the present invention are useful as CB-1 inverse agonists (or antagonists), certain classes are preferred, as for example, compounds having any of the following enumerated selections of substituents:

1) $R^1$ is —OCF$_3$, —OCHF$_2$, —CF$_3$ or —CN.
2) $R^1$ is —OCF$_3$, —OCHF$_2$ or —CF$_3$.
3) $R^1$ is —OCF$_3$ or —OCHF$_2$.
4) $R^1$ is —OCF$_3$ or —CF$_3$.
5) $R^2$ is hydrogen, fluoro, chloro, cyano, trifluoromethyl, 1,1-difluoroethyl, trifluoromethoxy, difluoromethoxy, or 1,1,2,2-tetrafluoroethoxy.
6) $R^2$ is trifluoromethyl, 1,1-difluoroethyl, difluoromethoxy, trifluoromethoxy, or 1,1,2,2-tetrafluoroethoxy.
7) $R^2$ is trifluoromethyl, 1,1-difluoroethyl, difluoromethoxy, trifluoromethoxy, or 1,1,2,2-tetrafluoroethoxy, and $R^3$ is hydrogen.
8) $R^2$ is —OCF$_3$ or —CF$_3$.
9) $R^2$ is —OCF$_3$ or —CF$_3$ and $R^3$ is hydrogen.
10) $R^2$ is —OCF$_3$, —OCHF$_2$, or 1,1,2,2-tetrafluoroethoxy.
11) $R^2$ is —OCF$_3$, —OCHF$_2$, or 1,1,2,2-tetrafluoroethoxy, and $R^3$ is hydrogen.
12) $R^3$ is hydrogen.
13) $R^4$ is —CF$_3$.
14) $R^1$ is —OCF$_3$, —OCHF$_2$, and $R^2$ is hydrogen, fluoro, chloro, cyano, trifluoromethyl, 1,1-difluoroethyl, trifluoromethoxy, difluoromethoxy, or 1,1,2,2-tetrafluoroethoxy.
15) $R^1$ is —OCF$_3$, —OCHF$_2$, and $R^2$ is trifluoromethyl, 1,1-difluoroethyl, trifluoromethoxy, difluoromethoxy, or 1,1,2,2-tetrafluoroethoxy, and $R^3$ is hydrogen.
16) $R^1$ is —OCF$_3$, —CF$_3$ or —CN; $R^2$ is hydrogen, —OCF$_3$ or —CF$_3$; $R^3$ is hydrogen; and $R^4$ is —CF$_3$.
17) $R^1$ is —OCF$_3$ or —CF$_3$; $R^2$ is hydrogen, —OCF$_3$ or —CF$_3$; $R^3$ is hydrogen; and $R^4$ is —CF$_3$.
18) $R^1$ is —OCF$_3$, —CF$_3$ or —CN; $R^2$ is —OCF$_3$ or —CF$_3$; $R^3$ is hydrogen; and $R^4$ is —CF$_3$.
19) $R^1$ is —OCF$_3$ or —CF$_3$; $R^2$ is —OCF$_3$ or —CF$_3$; $R^3$ is hydrogen; and $R^4$ is —CF$_3$.

Specific preferred compounds of the present invention are those described in the Examples herein, including the free bases and the pharmaceutically acceptable salts thereof.

General Schemes

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. All substituents, unless otherwise indicated, are as previously defined, and all reagents are well known and appreciated in the art.

Scheme I

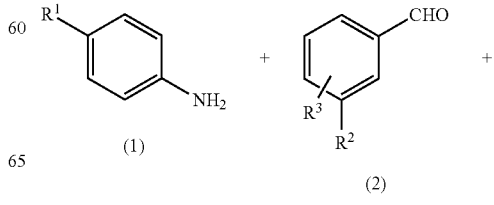

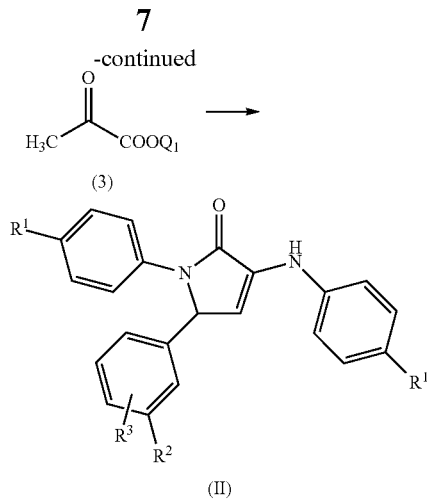

In Scheme I, a compound of Formula (II) may be prepared by the method described by Andreichikov and coworkers (Andreichikov, et al. Zhurnal Organicheskoi Khimii 22(10), 2208-13 (1986)), in which a mixture of an amine of Formula (1) and an aldehyde of Formula (2) is treated with an ester of pyruvic acid (3), where $Q_1$ is a $C_{1-3}$ alkyl group, in a suitable solvent such as glacial HOAc. Suitable esters of pyruvic acid include ethyl pyruvate. The reaction may proceed at temperatures between room temperature and the boiling point of the solvent. In some cases, the product (II) may precipitate during the course of the reaction or upon addition of a solvent in which the product is not highly soluble. These solvents include isopropyl alcohol and water and mixtures thereof. If a precipitate is formed, the compound of Formula (II) may be isolated by filtration and vacuum drying or by filtration and chromatography. Alternatively, the compound may be isolated by concentration of the reaction and chromatography of the residue or by aqueous workup and concentration and chromatography of the organic extracts.

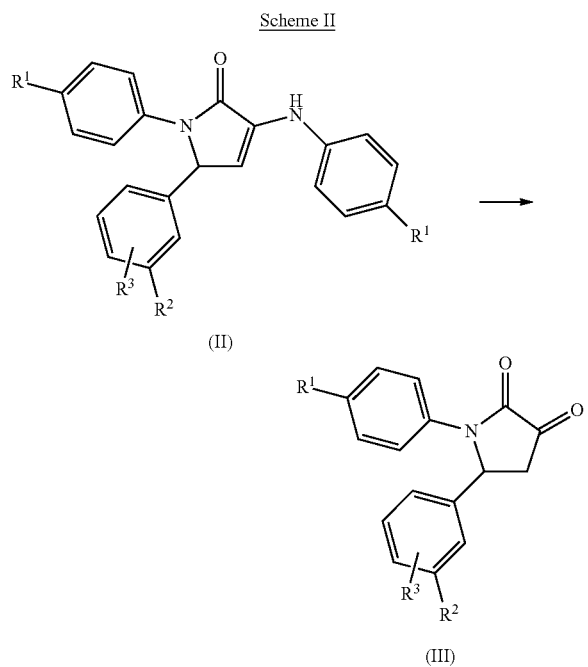

In Scheme II, a compound of formula (III) may be prepared by treatment of a compound of formula (II) with water, optionally in the presence of an acid. This reaction may also optionally be performed in the presence of additional solvents such as tetrahydrofuran, acetic acid and ethanol or mixtures thereof. A suitable acid includes trifluoroacetic acid and hydrochloric acid. It is often advantageous to perform this reaction in the presence of at least one equivalent of 2,5-dimethoxytetrahydrofuran. Once the compound of formula (III) has formed, it can be isolated by adding water and cooling to form a precipitate and subsequent isolation of the precipitate through filtration or by adding a mixture of solvents such as toluene and isopropyl acetate and washing with water and saturated aqueous sodium bicarbonate solution. The organic layer may be dried over a desiccant such as sodium sulfate and concentrated to provide the product as a crude mixture. The organic layer also may be used directly in the next reaction without further concentration or purification.

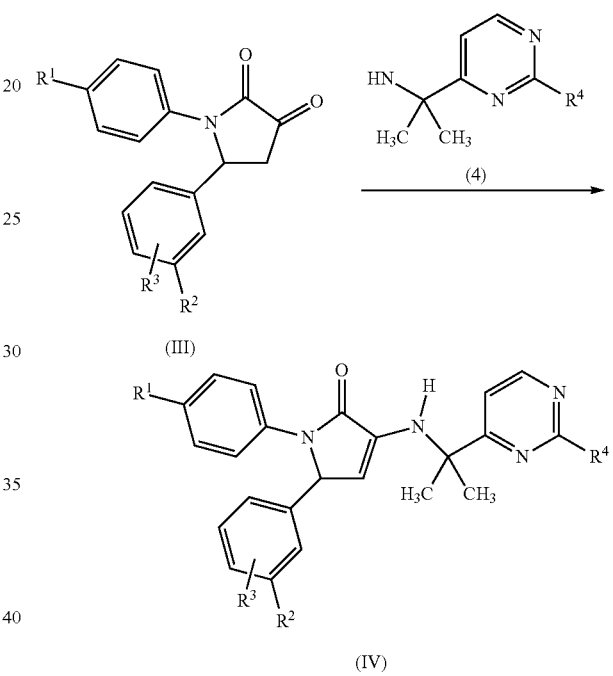

In Scheme III, a compound of Formula (IV) may be prepared by treatment of a solution of a compound of Formula (III) with a compound of Formula (4) in a suitable solvent such as toluene, methanol, isopropyl acetate or a mixture of the solvents. This reaction may also be performed in the presence of a catalyst such as HOAc. The compound of Formula (IV) can be isolated, if desired, by methods known in the art such as by precipitation or by silica gel chromatography.

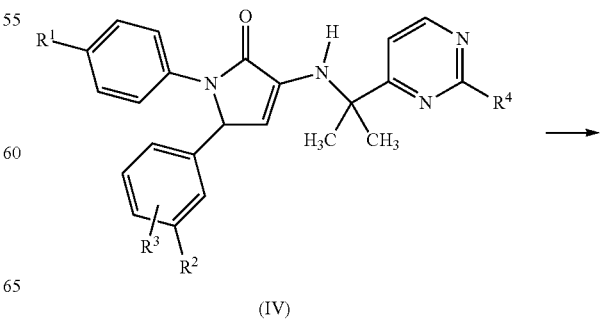

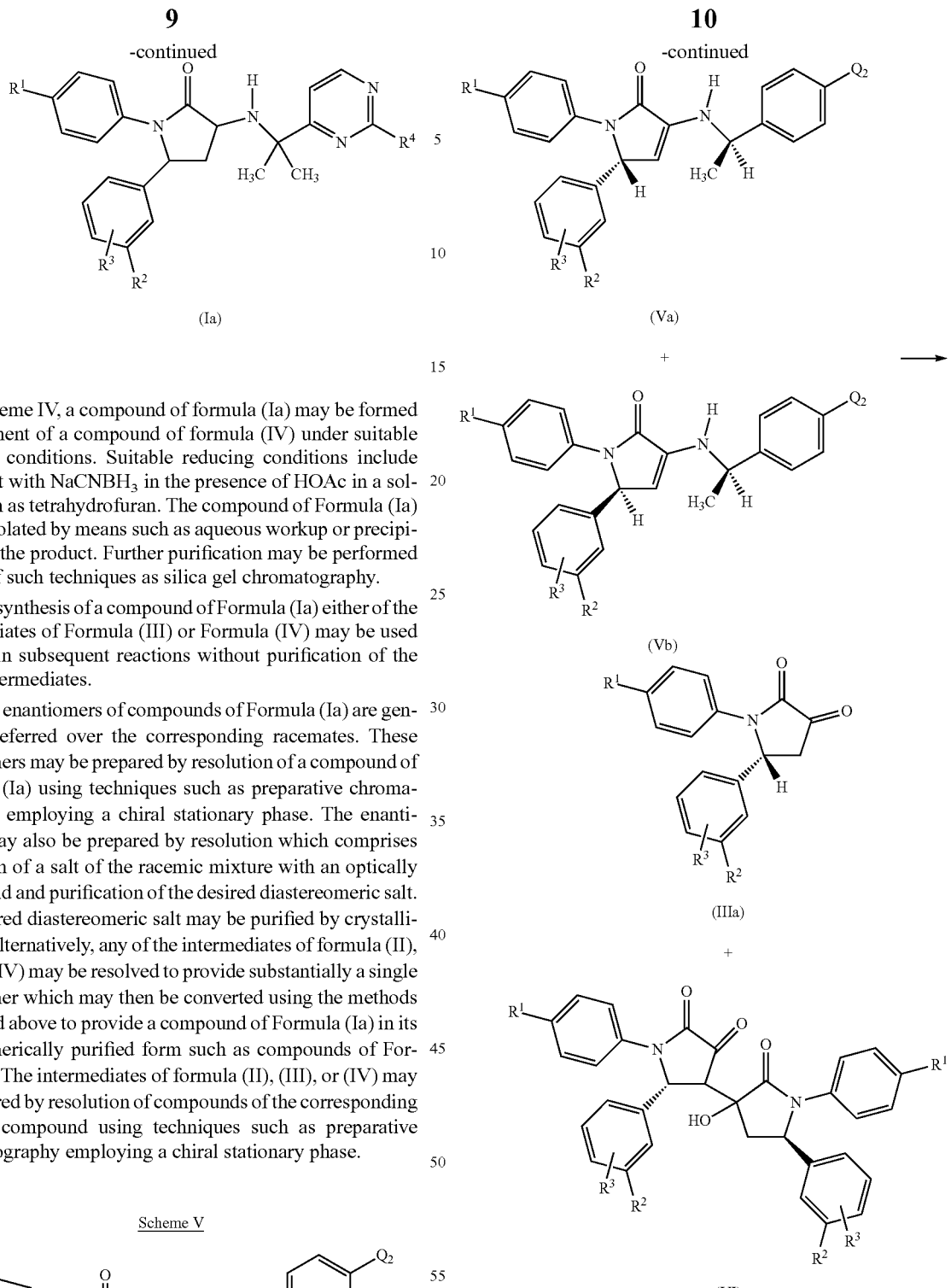

In Scheme IV, a compound of formula (Ia) may be formed by treatment of a compound of formula (IV) under suitable reducing conditions. Suitable reducing conditions include treatment with $NaCNBH_3$ in the presence of HOAc in a solvent such as tetrahydrofuran. The compound of Formula (Ia) can be isolated by means such as aqueous workup or precipitation of the product. Further purification may be performed by use of such techniques as silica gel chromatography.

In the synthesis of a compound of Formula (Ia) either of the intermediates of Formula (III) or Formula (IV) may be used directly in subsequent reactions without purification of the crude intermediates.

Single enantiomers of compounds of Formula (Ia) are generally preferred over the corresponding racemates. These enantiomers may be prepared by resolution of a compound of Formula (Ia) using techniques such as preparative chromatography employing a chiral stationary phase. The enantiomers may also be prepared by resolution which comprises formation of a salt of the racemic mixture with an optically active acid and purification of the desired diastereomeric salt. The desired diastereomeric salt may be purified by crystallization. Alternatively, any of the intermediates of formula (II), (III), or (IV) may be resolved to provide substantially a single enantiomer which may then be converted using the methods described above to provide a compound of Formula (Ia) in its enantiomerically purified form such as compounds of Formula (I). The intermediates of formula (II), (III), or (IV) may be prepared by resolution of compounds of the corresponding racemic compound using techniques such as preparative chromatography employing a chiral stationary phase.

Scheme V

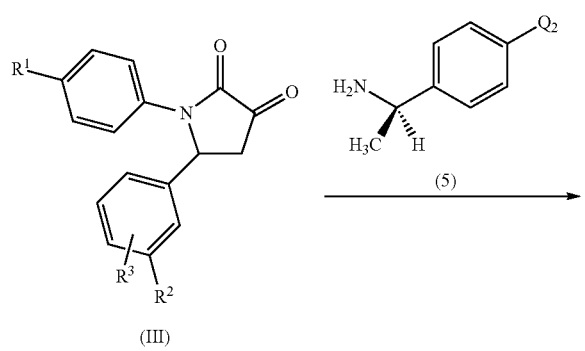

An alternative and often preferred method for the preparation of purified enantiomers of compounds of formula (III) is outlined in Scheme V. A racemic compound of formula (III) is reacted with a compound of formula (5), in which $Q_2$ is hydrogen or halo to form a diastereomeric mixture of compounds of formula (Va) and (Vb). Preferred compounds of formula (5) include R-alpha-methylbenzylamine or S-alpha-methylbenzylamine. This condensation may be performed such as described in previously in Scheme III by combining a compound of Formula (III) and compound (5) an inert solvent. This reaction may also be performed in the presence of a catalyst such as HOAc. The diastereomers of formula (Va) and (Vb) are then separated using techniques such as silica gel chromatography or crystallization from inert solvents such as isopropanol, or methanol/KOH. The desired diastereomer (designated (Va)) in Scheme V is then hydrolyzed to form the purified enantiomer of formula (IIIa). Suitable hydrolysis conditions include treating a solution of the desired diastereomer in HOAc with aqueous hydrochloric acid or trifluoroacetic acid and water and optionally, 2,5-dimethoxytetrahydrofuran. In some instances, the crude (IIIa) may contain substantial amounts of the dimer of formula (VI).

In Scheme V, the racemic compound of formula (III) may be crude product resulting from the process outlined in Scheme II. In addition, the purified enantiomer (optionally containing (VI)) of formula (Ma) may be used directly from the hydrolysis reaction, without further purification, in the process outlined in Scheme III.

In Scheme V, the (R)-enantiomer of compound (5) was chosen to exemplify the process. One skilled in the art will recognize that the (S)-enantiomer of compound (5) may also be used in this process. The choice of whether to use the (R) or (S)-enantiomer may be made depending on which will yield the desired diastereomer that is more readily isolated.

Scheme VI

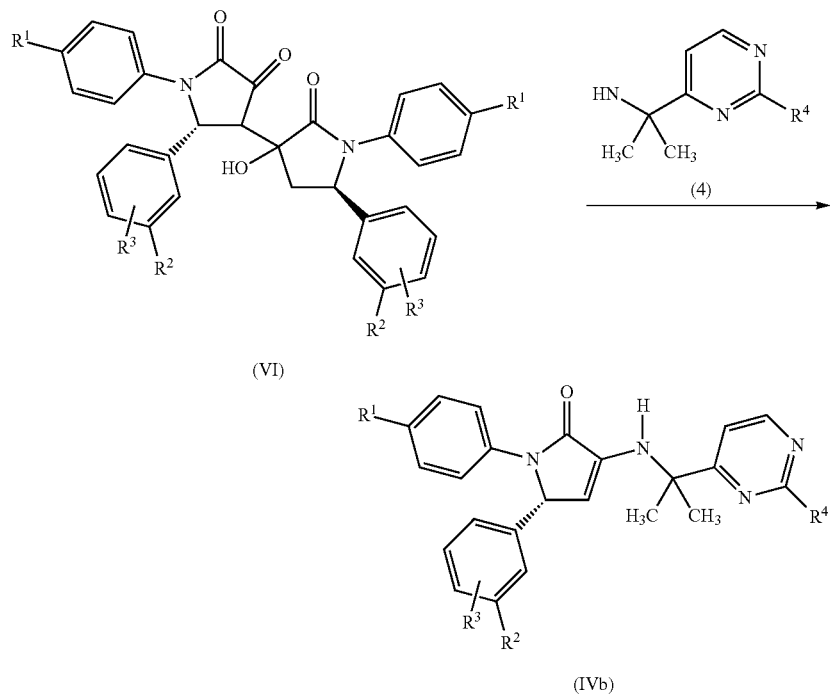

(VI)

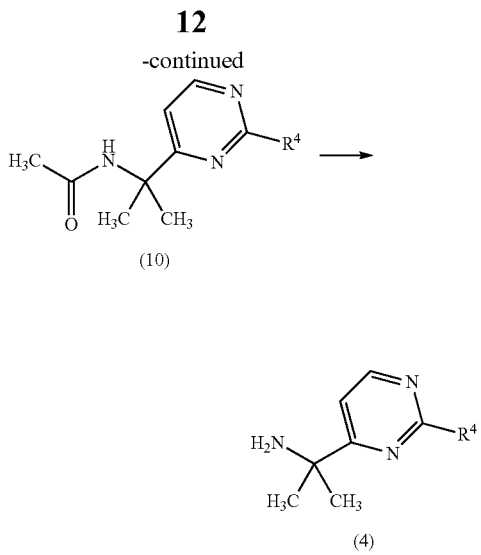

In Scheme VI, the compound of formula (IVb) may also be formed by treatment of compound of formula (VI) with compound (4) under the same conditions as described for the reaction of compound (III) with (4)(Scheme III).

Scheme VII

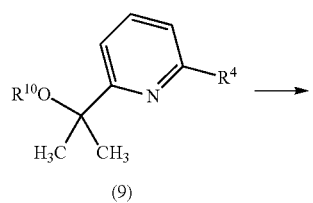

(9)

In Scheme VII, the compound (4) is prepared by treatment of a compound (9), in which $R^{10}$ is hydrogen, —$CH_3$, —$CH_2CH_3$ or —$C(O)CH_3$ with acetonitrile in the presence of acid to provide a compound of Formula (10). Suitable acids include sulfuric acid or a suitable Lewis acid such as boron trifluoride etherate. After combining the above, the reaction is heated, cooled to about room temperature, and quenched with aqueous sodium hydroxide. Compound (10) is isolated by traditional means such as extraction with a suitable solvent such as ethyl acetate and concentration of the organic layer. Compound (10) is heated in a solution of aqueous hydrochloric acid to around 100° C. The compound is extracted with diethyl ether. The aqueous layer is made alkaline with aqueous sodium hydroxide and extracted with diethyl ether. The organic layers are combined, dried over sodium sulfate, filtered, and concentrated to give compound (4).

PREPARATIONS AND EXAMPLES

Conditions for High Performance Liquid Chromatography (HPLC) Methods referred to throughout the Preparations and Examples Method 1
LC Column. Phenomenex® Gemini® $C_{18}$ 2.0×50 mm 3 OnM
Gradient: 5-100% acetonitrile w/0.1% formic acid in 7.0 min. then held at 100% for 1.0 min.
Column temperature: 50° C.+/−10° C.
Autosampler temperature: ambient
Flow Rate: 1.0 mL/min.
Signal detected at 214 and 300 nM wavelength.
Method 2
LC Column. Phenomenex® Gemini® $C_{18}$ 2.0×50 mm 3.0 μm
Gradient: 5-100% acetonitrile w/0.1% formic acid in 3.5 min then held at 100% for 0.5 min
Column temperature: 50° C.+/−10° C.
Autosampler temperature: ambient
Flow Rate: 1.0 mL/min
Signal detected at 214 and 300 nM wavelength.
Method 3
LC column. Zorbax® RX-$C_{18}$ 4.6×250 mm 5 μm
Gradient: 50-90% acetonitrile w/0.03 M Phosphate Buffer (Phosphate Buffer=5.52 g $NaH_2PO_4$ and 1.4 mL $H_3PO_4$ in 2 L Milli-Q $H_2O$) in 15 minutes.
Column temperature: 40° C.
Autosampler temperature: ambient
Flow rate: 1.5 mL/min.
Signal detected at 260 nM wavelength.
Method 4
LC column. Zorbax® SB-phenyl 4.6×150 mm 5 μm
Isocratic: 36% A and 64% B, where A=0.05 M $NH_4OAc$ in water (pH 5.0) and B=acetonitrle for 10 minutes.
Column temperature: 35° C.
Autosampler temperature: ambient
Flow rate: 2.0 mL/min.
Signal detected at 206 nM wavelength.

Preparation 1: (±)-5-(3-Trifluoromethoxy-phenyl)-1-(4-trifluoromethyl-phenyl)-3-(4-trifluoromethyl-phenylamino)-1,5-dihydro-pyrrol-2-one

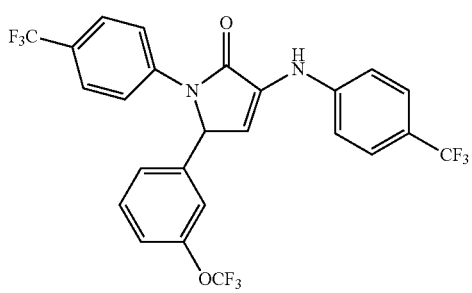 [SMILES: O=C1C(Nc2ccc(C(F)(F)F)cc2)=CC(c2cccc(OC(F)(F)F)c2)N1c1ccc(C(F)(F)F)cc1]

Stir 3-(trifluoromethoxy)-benzaldehyde (25.0 g, 132 mmol) and ethyl pyruvate (15.3 g, 132 mmol) in glacial acetic acid (125 mL) at ambient temperature for 10 minutes. Add 4-(trifluoromethyl)aniline (46.7 g, 290 mmol) drop-wise over 15 minutes with continued stirring, warm the solution to 30° C., and stir for about 22 h. Cool the solution to 26° C., add isopropanol (125 mL) and water (125 mL). Stir the solution at room temperature for 15 minutes, filter the precipitate and wash with a 1:1 mixture of iso-propyl alcohol-water (100 mL×2). Dry under vacuum at 40° C. to afford (±)-5-(3-trifluoromethoxy-phenyl)-1-(4-trifluoromethyl-phenyl)-3-(4-trifluoromethyl-phenylamino)-1,5-dihydro-pyrrol-2-one (60.46 g, 84%) as a white powder: LC-MS ESI m/z: 545.1 (M−H)$^−$, Rt=10.9 min., method 3. $^1$H NMR (500 MHz, DMSO-$d_6$) δ 8.76 (s, 1H), 7.86 (d, 2H, J=8.5 Hz), 7.70 (d, 2H, J=8.5 Hz), 7.56 (d, 2H, J=9.0 Hz), 7.47 (d, 2H, J=8.5 Hz), 7.44-7.41 (m, 1H), 7.37 (s, 1H), 7.29 (d, 1H, J=8.0 Hz), 7.22 (d, 1H, J=8.0 Hz), 6.66 (d, 1H, J=3.0 Hz), 6.29 (d, 1H, J=2.5 Hz).

Preparation 2: (±)-5-Phenyl-1-(4-trifluoromethoxy-phenyl)-3-(4-trifluoromethoxy-phenylamino)-1,5-dihydro-pyrrol-2-one

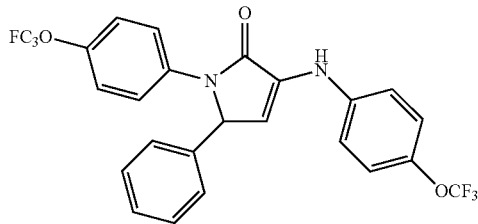

Add 4-(trifluoromethoxy)aniline (1.86 L, 13.75 mol) in portions to a solution of benzaldehyde (559 mL, 5.50 mol), and ethyl pyruvate (605 mL, 5.50 mol) in glacial acetic acid (5.0 L). Observe exotherm to 43° C. Stir at ambient temperature for 18 hours. Filter the precipitate, and wash the wet cake with glacial acetic acid (500 mL). Dry under vacuum for 3 hours to afford (±)-5-phenyl-1-(4-trifluoromethoxy-phenyl)-3-(4-trifluoromethoxy-phenylamino)-1,5-dihydro-pyrrol-2-one (1999 g, 74%) as a white crystalline solid. $^1$H NMR (400 MHz, DMSO-$d_6$) δ 8.43 (s, 1H), 7.74 (d, J=12 Hz, 2H), 7.19-7.38 (m, 11H), 6.42 (s, 1H), 6.08 (s, 1H). LC-MS ESI m/z: 495.0 (M+1)$^+$, 493.0 (M−1)$^−$, $T_r$=6.60 min., method 1.

Preparation 3: (±)-5-(3-Fluoro-phenyl)-1-(4-trifluoromethoxy-phenyl)-3-(4-trifluoromethoxy-phenylamino)-1,5-dihydro-pyrrol-2-one

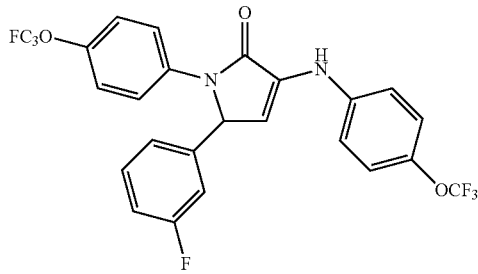

Mix 3-fluorobenzaldehyde (10.0 mL, 94.3 mmol), 4-(trifluoromethoxy)aniline (31.9 mL, 235.7 mmol) and ethyl pyruvate (10.4 mL, 94.3 mmol) in glacial acetic acid (150 mL). Stir at ambient temperature for 18 hours. Filter the precipitate, and wash with hexanes to afford (±)-5-(3-fluoro-phenyl)-1-(4-trifluoromethoxy-phenyl)-3-(4-trifluoromethoxy-phenylamino)-1,5-dihydro-pyrrol-2-one (23.4 g, 48%). LC-MS ESI m/z: 511 (M−1)$^−$, $T_r$=5.45 min., method 1.

Preparation 4: 1-(4-Trifluoromethylphenyl)-3-[(1R)-1-(4-chlorophenyl)-ethylamino]-5(R)-(3-trifluoromethoxyphenyl)-1,5-dihydropyrrol-2-one

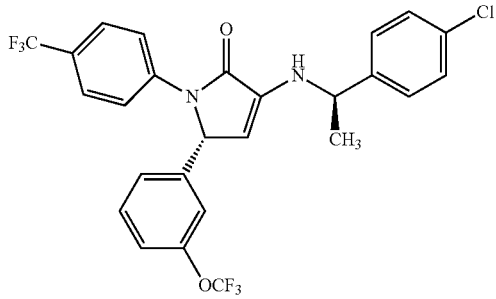 [SMILES: C[C@@H](NC1=C[C@H](c2cccc(OC(F)(F)F)c2)N(c2ccc(C(F)(F)F)cc2)C1=O)c1ccc(Cl)cc1]

Mix ethanol (120 mL), glacial acetic acid (15 mL), water (3.0 mL, 164.7 mmol), trifluoroacetic acid (6.2 mL, 82.4 mmol), (±)-5-(3-trifluoromethoxy-phenyl)-1-(4-trifluoromethyl-phenyl)-3-(4-trifluoromethyl-phenylamino)-1,5-dihydro-pyrrol-2-one (30.0 g, 54.9 mmol), and 2,5-dimethoxytetrahydrofuran (10.7 mL, 82.4 mmol). Warm the solution to 50° C. and stir the reaction mixture for about 18 hours. Discontinue heating the solution, add water (35 mL), and cool the reaction mixture to −19° C. Filter the slurry and wash the solid with a 1:4 mixture of water-methanol (20 mL). Transfer the filtrate to a separatory funnel and wash with 6% brine (280 mL), add 6% brine (100 mL), methanol (40 mL), diethyl ether (100 mL), and saturated sodium bicarbonate solution (43 mL) to the organic phase. Separate the layers, add methanol (60 mL) to the organic phase, and concentrate the solution to approximately 1 volume containing (±)-5-(3-trifluoromethoxy-phenyl)-1-(4-trifluoromethyl-phenyl)-pyrrolidine-2,3-dione. Add methanol (60 mL) and (R)-4-chloro-alpha-methylbenzylamine (7.8 mL, 55.0 mmol) and stir at room temperature for 24 hours. Monitor the reaction by HPLC for completion (Method 4), then cool the solution to −7° C. and continue stirring at this temperature for 72 hours. Add a pre-mixed solution of potassium hydroxide (0.69 g, 10.5 mmol) in methanol (11 mL) to the reaction mixture, warm the solution to 10° C., and stir for an additional 4 hours. Cool the solution to −7° C., filter the slurry, and rinse the resultant product with methanol (5 mL×3). Dry the solid under vacuum to obtain 1-(4-trifluoromethyl-phenyl)-3-[1 (R)-(4-chloro-phenyl)-ethylamino]-5 (R)-(3-trifluoromethoxy-phenyl)-1,5-dihydro-pyrrol-2-one (12.3 g, 47.7%) as a white solid: LC-MS ESI m/z: 539.0 (M−H)$^-$, $T_r$=4.3 min., method 4. $^1$H NMR (500 MHz, DMSO-d$_6$) δ 7.76 (d, 2H, J=8.5 Hz), 7.62 (d, 2H, J=9.0 Hz), 7.38-7.36 (m, 2H), 7.30-7.27 (m, 3H), 7.10 (dd, 1H, J=8.5, 1.0 Hz), 7.05 (d, 1H, J=7.5 Hz), 6.95 (s, 1H), 6.06 (d, 1H, J=8.0 Hz), 5.96 (d, 1H, J=3.0 Hz), 5.22 (d, 1H, J=3.0 Hz), 4.35-4.32 (m, 1H), 1.43 (d, 3H, J=6.5 Hz).

Preparation 5: 1-(4-Trifluoromethoxy-phenyl)-3-((R)-1-phenyl-ethylamino)-5(R)-phenyl-1,5-dihydro-pyrrol-2-one

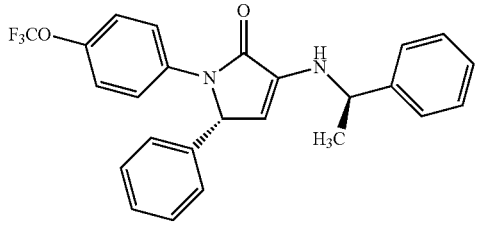 [SMILES: C[C@@H](NC1=C[C@H](c2ccccc2)N(c2ccc(OC(F)(F)F)cc2)C1=O)c1ccccc1]

Add acetic acid (464 mL, 8.09 mol), 2,5-dimethoxytetrahydrofuran (393 mL, 3.03 mol), water (2.27 L), and trifluoroacetic acid (153 mL, 2.02 mol) sequentially to a solution of (±)-5-phenyl-1-(4-trifluoromethoxy-phenyl)-3-(4-trifluoromethoxy-phenylamino)-1,5-dihydro-pyrrol-2-one (1000 g, 2.02 mol) in THF (8.43 L). Stir the reaction mixture at ambient temperature for 18 hours. Add toluene (4.0 L) and isopropyl acetate (2.0 L). Wash the mixture with water (8.0 L) and saturated sodium hydrogencarbonate solution (6.0 L). Discard the aqueous layer. To the organic layer, add (R)-(+)-α-methyl benzylamine (390 mL, 3.03 mol). Stir the solution at ambient temperature for 3 hours. Concentrate the reaction mixture to obtain a mixture of 1-(4-trifluoromethoxy-phenyl)-3-((R)-1-phenyl-ethylamino)-(5)-(S)-phenyl-1,5-dihydro-pyrrol-2-one and 1-(4-trifluoromethoxy-phenyl)-3-((R)-1-phenyl-ethylamino)-(R)-5-phenyl-1,5-dihydro-pyrrol-2-one as a black oil. Dissolve the mixture (888 g, 2.02 mol) in isopropanol (2.0 L) and cool to −7° C. Filter the precipitate and wash with cold isopropanol. Dry under vacuum for 12 hours to give 1-(4-trifluoromethoxy-phenyl)-3-((R)-1-phenyl-ethylamino)-(R)-5-phenyl-1,5-dihydro-pyrrol-2-one (130 g, 29%) as an off-white solid. $^1$H NMR (400 MHz, DMSO-d$_6$) δ 7.64 (d, J=8 Hz, 2H), 7.34 (d, J=8 Hz, 2H), 7.24 (m, 4H), 7.11 (m, 4H), 6.98 (d, J=4 Hz, 2H), 5.78 (m, 2H), 5.13 (s, 1H), 4.30 (m, 1H), 1.44 (d, J=4 Hz 3H). LC-MS ESI m/z: 439 (M+H)$^+$, $T_r$=6.30 min., method 1.

Preparation 6: 1-(4-Trifluoromethoxy-phenyl)-3-(R)-1-phenyl-ethylamino)-5(R)-(3-fluoro-phenyl)-1,5-dihydro-pyrrol-2-one

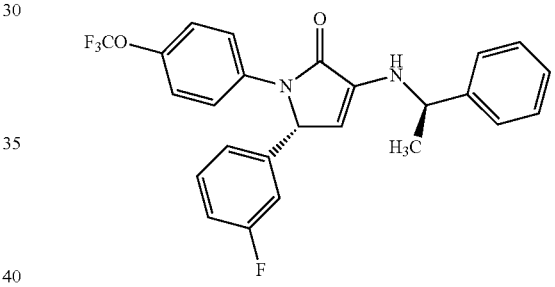

Add water (46.8 mL, 2.6 mol), acetic acid (10.5 mL, 182.7 mmol), trifluoroacetic acid (6.9 mL, 91.3 mol), and 2,5-dimethoxytetrahydrofuran (6.5 mL, 50.2 mmol) to a solution of (±)-5-(3-fluoro-phenyl)-1-(4-trifluoromethoxy-phenyl)-3-(4-trifluoromethoxy-phenylamino)-1,5-dihydro-pyrrol-2-one (23.4 g, 45.7 mmol) in THF (45 mL). Stir the reaction mixture at 30° C. for 18 hours. Observe significant formation of (R)-5-(3-fluoro-phenyl)-1-(4-trifluoromethoxy-phenyl)-pyrrolidine-2,3-dione (LC-MS ESI m/z: 352 (M−H)$^-$, method 1). Pour the reaction mixture into toluene (200 mL), isopropyl acetate (50 mL) and water (100 mL) and stir for 5 min. Separate the layers and wash the organic layer with water (50 mL) and 5% sodium hydrogencarbonate solution (50 mL). To the organic layer, add (R)-(+)-α-methyl benzylamine (7.7 mL, 59.9 mmol). Stir the solution at ambient temperature for 18 hours. Add (R)-(+)-α-methyl benzylamine (3.0 mL, 24.8 mmol) and heat to 30° C. for 3 hours. Wash the reaction mixture with water and brine. Concentrate the reaction mixture to obtain a mixture of 1-(4-trifluoromethoxy-phenyl)-3-((R)-1-phenyl-ethylamino)-5(S)-(3-fluoro-phenyl)-1,5-dihydro-pyrrol-2-one and 1-(4-trifluoromethoxy-phenyl)-3-((R)-1-phenyl-ethylamino)-5 (R)-(3-fluoro-phenyl)-1,5-dihydro-pyrrol-2-one. Dissolve the mixture in isopropanol (70 mL) and stir at ambient temperature for 72 hours. Filter the precipitate and wash with isopropanol to give 1-(4-trifluoromethoxy-phenyl)-3-((R)-1-phenyl-ethylamino)-5 (R)-(3-fluoro-phenyl)-1,5-dihydro-pyrrol-2-one (6.30 g, 30%) as a white solid. LC-MS ESI m/z: 457 (M+H)$^+$, $T_r$=5.13 min., method 1

Preparation 7: 2-(2-Trifluoromethyl-pyrimidin-4-yl)-propan-2-ol

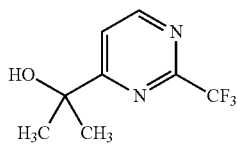

Cool a solution of THF (200 mL) and methylmagnesium bromide (3.0 M in diethyl ether, 81 mL, 243 mmol) to 0° C. Add a solution of trifluoromethylpyrimidine-4-carboxylic acid methyl ester (16.7 g, 81 mmol) in THF (100 mL) over a period of 5 min. Stir for 30 min at 0° C. then slowly pour into saturated aqueous ammonium chloride. Extract the aqueous layer with diethyl ether, combine the organic layers, dry over sodium sulfate, filter, and concentrate under reduced pressure to give 2-(2-trifluoromethyl-pyrimidin-4-yl)-propan-2-ol (16.7 g, 100%) as a clear, colorless oil. MS (m/z): 207.2 (M+H)$^+$.

Preparation 8: N-[1-Methyl-1-(2-trifluoromethyl-pyrimidin-4-yl)-ethyl]-acetamide

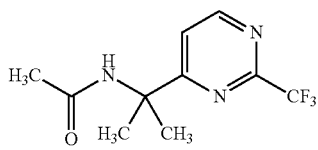 [SMILES: CC(=O)NC(C)(C)c1ccnc(C(F)(F)F)n1]

Heat a solution of acetonitrile (300 mL) and 2-(2-trifluoromethyl-pyrimidin-4-yl)-propan-2-ol (16.5 g, 80 mmol) to 90° C. In a separate reaction vessel, cool acetonitrile (70 mL) to 0° C. and add sulfuric acid (19.2 mL, 360 mmol) at such a rate that the temperature does not exceed 10° C. Add the cooled sulfuric acid solution to the heated solution of 2-(2-trifluoromethyl-pyrimidin-4-yl)-propan-2-ol and acetonitrile and stir at 90° C. for 60 minutes. Cool to room temperature, concentrate to about ⅓ original volume, and add aqueous 5N NaOH (150 mL). Partition between ethyl acetate and brine then extract the aqueous layer with ethyl acetate (3×). Concentrate under reduced pressure the combined organic layers to yield N-[1-methyl-1-(2-trifluoromethyl-pyrimidin-4-yl)-ethyl]-acetamide (15.4 g, 78%) as a yellow solid. MS (m/z): 248.0 (M+H)$^+$.

Preparation 9: 1-Methyl-1-(2-trifluoromethyl-pyrimidin-4-yl)-ethylamine

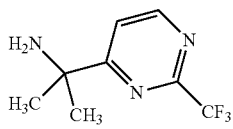

Heat a solution of N-[1-methyl-1-(2-trifluoromethyl-pyrimidin-4-yl)-ethyl]-acetamide (15.4 g, 62 mmol) and aqueous 5N HCl (150 mL) to 100° C. for 20 hours then cool to room temperature. Extract the reaction with diethyl ether (2×) then make the aqueous layer alkaline with aqueous 5N NaOH. Extract the aqueous layer with diethyl ether (3×), dry the combined organic layers over sodium sulfate, filter, and concentrate under reduced pressure to give 1-methyl-1-(2-trifluoromethyl-pyrimidin-4-yl)-ethylamine (7.2 g, 56%) as a brown oil. $^1$H NMR (400 MHz, CDCl$_3$): δ 8.80 (d, J=5.3 Hz, 1H), 7.68 (d, J=5.3 Hz, 1H), 1.76 (br s, 2H), 1.49 (s, 6H).

Preparation 10: (E)-4-Ethoxy-2-oxo-but-3-enoic acid ethyl ester

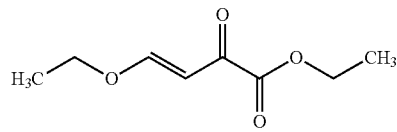

Reference: Dujardin, G; Rossignol, S.; Brown, E. Synthesis, 1998, 763-770. Add ethyl chlorooxoacetate (67 mL, 600 mmol) to a solution of palladium acetate (1.35 g, 6 mmol), ethyl vinyl ether (315 mL, 3.3 mol), and triethylamine (125 mL, 900 mmol) at ambient temperature. Heat to 55° C. for 24 hours, cool to room temperature, then partition the reaction mixture between diethyl ether and water. Concentrate under reduced pressure the organic layer to obtain (E)-4-ethoxy-2-oxo-but-3-enoic acid ethyl ester (72 g, 70%) as a brown oil. $^1$H NMR (400 MHz, CDCl$_3$): δ 7.84 (d, J=13.2 Hz, 1H), 6.15 (d, J=13.2 Hz, 1H), 4.29 (q, J=7.6 Hz, 2H), 4.03 (q, J=6.8 Hz, 2H), 1.34 (m, 6H).

Preparation 11: 2-Cyclopropyl-pyrimidine-4-carboxylic acid ethyl ester

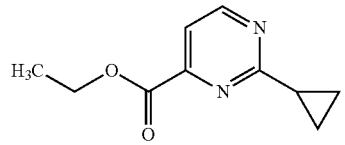

Reference: Riley, T. A.; Hennen, W. J.; Dalley, N. K.; Wilson, B. E.; J. Heterocyclic Chem., 1987, 24, 955-964. Heat a mixture of cyclopropylcarbamidine hydrochloride (2.05 g, 17 mmol), (E)-4-ethoxy-2-oxo-but-3-enoic acid ethyl ester (4.39 g, 25.5 mmol), ethanol (12 mL), and sodium ethoxide (1.16 g, 17 mmol) in a microwave at 140° C. for 20 min. Concentrate the reaction mixture under reduced pressure and partition the residue between ethyl acetate and brine. Separate the organic layer and concentrate under reduced pressure. Purify the residue by silica gel chromatography (10-30% ethyl acetate/hexane) to give 2-cyclopropyl-pyrimidine-4-carboxylic acid ethyl ester (1.5 g, 46%) as light yellow oil. MS (m/z): 193.0 (M+H)$^+$.

Preparation 12: 2-(2-Cyclopropyl-pyrimidin-4-yl)-propan-2-ol

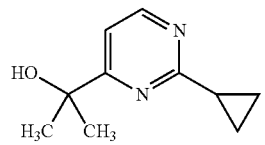

Cool a solution of THF (150 mL) and methylmagnesium bromide (3.0 M in diethyl ether, 52 mL, 243 mmol) to 0° C. Add a solution of 2-cyclopropyl-pyrimidine-4-carboxylic acid ethyl ester (9.9 g, 52 mmol) in THF (50 mL) over a period of 5 min. Stir for 45 min at 0° C. then slowly pour into saturated aqueous ammonium chloride. Extract the aqueous layer with diethyl ether, dry the combined organic layers over sodium sulfate, filter and concentrate under reduced pressure to give 2-(2-cyclopropyl-pyrimidin-4-yl)-propan-2-ol (9.15 g, 100%) as an orange solid. MS (m/z): 179.0 (M+H)+.

Preparation 13: N-[1-(2-Cyclopropyl-pyrimidin-4-yl)-1-methyl-ethyl]-acetamide

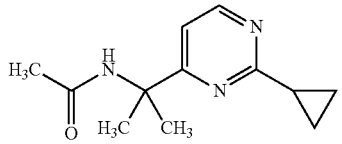 [SMILES: CC(=O)NC(C)(C)c1ccnc(C2CC2)n1]

Heat a solution of acetonitrile (150 mL) and 2-(2-cyclopropyl-pyrimidin-4-yl)-propan-2-ol of (8.85 g, 50 mmol) to 90° C. In a separate reaction vessel, cool acetonitrile (50 mL) to 0° C. and add sulfuric acid (11.9 mL, 223 mmol) at such a rate that the temperature does not exceed 10° C. Add the cooled sulfuric acid solution to the heated solution of 2-(2-cyclopropyl-pyrimidin-4-yl)-propan-2-ol and acetonitrile and stir at 95° C. for 4 days. Cool to room temperature and add aqueous 5N NaOH (100 mL). Extract the aqueous layer with ethyl acetate (3×). Concentrate under reduced pressure the combined organic layers to yield N-[1-(2-cyclopropyl-pyrimidin-4-yl)-1-methyl-ethyl]-acetamide (4.5 g, 41%) as a yellow oil. MS (m/z): 220.0 (M+H)+.

Preparation 14: 1-(2-Cyclopropyl-pyrimidin-4-yl)-1-methyl-ethylamine

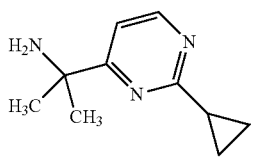

Heat a solution of N-[1-(2-cyclopropyl-pyrimidin-4-yl)-1-methyl-ethyl]-acetamide (4.5 g, 20.5 mmol) and aqueous 5N HCl (125 mL) to 100° C. for 18 hours. Cool the mixture to room temperature. Extract the reaction with diethyl ether (2×) then make the aqueous layer alkaline with aqueous 5N NaOH. Extract the aqueous layer with diethyl ether (3×), dry the combined organic layers over sodium sulfate, filter, and concentrate under reduced pressure to give 1-(2-cyclopropyl-pyrimidin-4-yl)-1-methyl-ethylamine (1.3 g, 36%) as a dark yellow oil. 1H NMR (400 MHz, CDCl3): δ 8.45 (d, J=5.6 Hz, 1H), 7.12 (d, J=5.6 Hz, 1H), 2.30 (m, 1H), 1.76 (br s, 2H), 1.41 (s, 6H), 1.09 (m, 2H), 1.02 (m, 2H).

Preparation 15: (R)-3-[1-Methyl-1-(2-trifluoromethyl-pyrimidin-4-yl)-ethylamino]-1-(4-trifluoromethyl-phenyl)-5-(3-trifluoromethoxy-phenyl)-1,5-dihydro-pyrrol-2-one

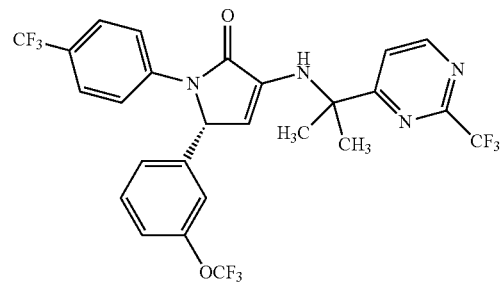 [SMILES: CC(C)(NC1=C[C@H](c2cccc(OC(F)(F)F)c2)N(c2ccc(C(F)(F)F)cc2)C1=O)c1ccnc(C(F)(F)F)n1]

Add trifluoroacetic acid (7.56 mL, 100 mmol) to a solution of 1-(4-trifluoromethyl-phenyl)-3-[(R)-1-(4-chloro-phenyl)-ethylamino]-5(R)-(3-trifluoromethoxy-phenyl)-1,5-dihydro-pyrrol-2-one (10.8 g, 20.0 mmol) in acetic acid (100 mL) and water (5 mL). Stir at ambient temperature for 60 min. Observe significant formation of (R)-5-(3-trifluoromethoxy-phenyl)-1-(4-trifluoromethyl-phenyl)-pyrrolidine-2,3-dione (LC-MS ESI m/z: 426 (M+Na)+, T$_r$=2.76 min., method 2). Dilute the reaction with toluene (200 mL) and water (150 mL). Wash the organic layer with water and saturated aqueous sodium bicarbonate solution. Filter the organic layer through sodium sulfate. Add acetic acid (9.17 mL, 160 mmol) and 1-methyl-1-(2-trifluoromethyl-pyrimidin-4-yl)-ethylamine (4.51 g, 22 mmol) to this toluene solution containing (R)-5-(3-trifluoromethoxy-phenyl)-1-(4-trifluoromethyl-phenyl)-pyrrolidine-2,3-dione. Heat to 55° C. for 18 hours. Concentrate reaction mixture under reduced pressure to give a dark purple oil. Purify the residue by silica gel chromatography (25% ethyl acetate-hexane) to obtain (R)-3-[1-methyl-1-(2-trifluoromethyl-pyrimidin-4-yl)-ethylamino]-1-(4-trifluoromethyl-phenyl)-5-(3-trifluoromethoxy-phenyl)-1,5-dihydro-pyrrol-2-one (7.70 g, 65%) as a purple foam. LC-MS ESI m/z: 613 (M+Na)+, T$_r$=3.35 min., method 2.

Preparation 16: (R)-3-[1-(2-Cyclopropyl-pyrimidin-4-yl)-1-methyl-ethylamino]-5-(3-trifluoromethoxy-phenyl)-1-(4-trifluoromethyl-phenyl)-1,5-dihydro-pyrrol-2-one

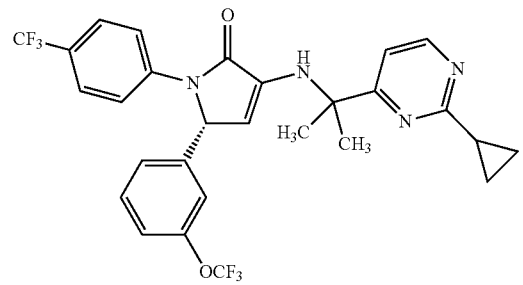 [SMILES: CC(C)(NC1=C[C@H](c2cccc(OC(F)(F)F)c2)N(c2ccc(C(F)(F)F)cc2)C1=O)c1ccnc(C2CC2)n1]

Prepare the title compound essentially as described in the method of Preparation 15 using 1-(2-cyclopropyl-pyrimidin-4-yl)-1-methyl-ethylamine Yield 38%, LC-MS ESI m/z: 563 (M+H)+, T$_r$=3.46 min, method 2.

Example 1

(3R,5R)-3-[1-Methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one

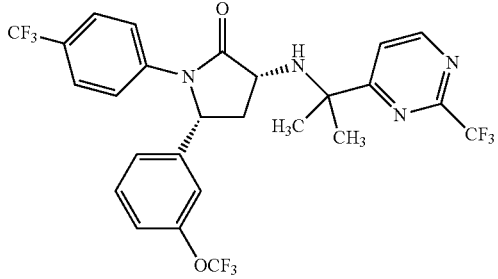 [SMILES: CC(C)(N[C@@H]1C[C@H](c2cccc(OC(F)(F)F)c2)N(c2ccc(C(F)(F)F)cc2)C1=O)c1ccnc(C(F)(F)F)n1]

Cool a solution of (R)-3-[1-methyl-1-(2-trifluoromethyl-pyrimidin-4-yl)-ethylamino]-1-(4-trifluoromethyl-phenyl)-5-(3-trifluoromethoxy-phenyl)-1,5-dihydro-pyrrol-2-one (7.5 g, 12.7 mmol) in acetic acid (60 mL) and THF (15 mL) to 0° C. and add sodium cyanoborohydride (1.60 g, 25.4 mmol). Remove the cooling bath after 5 minutes and stir 60 minutes at ambient temperature. Dilute the reaction mixture with ethyl acetate and slowly pour into saturated aqueous sodium bicarbonate solution. Separate the organic layer and concentrate under reduced pressure. Purify the residue by silica gel chromatography (15-40% ethyl acetate-hexane) to obtain (3R,5R)-3-[1-methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one (5.20 g, 69%) as a purple foam. To remove purple color, dissolve (3R,5R)-3-[1-methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one in methanol (150 mL) and add activated carbon. Stir at ambient temperature for 20 min, filter, and concentrate under reduced pressure to give a white foam (4.6 g, 88%). $^1$H NMR (400 MHz, CDCl$_3$): δ 8.79 (d, J=5.3 Hz, 1H), 7.90 (d, J=5.3 Hz, 1H), 7.46 (d, J=8.4 Hz, 2H), 7.36 (d, J=8.8 Hz, 2H), 7.27 (t, J=7.9 Hz, 1H), 7.08 (d, J=7.9 Hz, 1H), 7.04 (d, J=8.4 Hz, 1H), 6.98 (s, 1H), 5.04 (dd, J=6.2, 9.7 Hz, 1H), 3.51-3.45 (m, 1H), 2.90-2.81 (m, 1H), 1.89-1.81 (m, 1H), 1.56 (s, 3H), 1.50 (s, 3H). LC-MS ESI m/z: 593 (M+H)$^+$, T$_r$=3.07 min., method 2.

Example 2

(3R,5R)-3-[1-(2-Cyclopropyl-pyrimidin-4-yl)-1-methyl-ethylamino]-5-(3-trifluoromethoxy-phenyl)-1-(4-trifluoromethyl-phenyl)-pyrrolidin-2-one

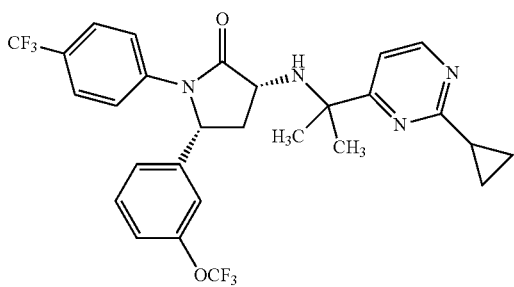

Prepare the title compound essentially as described for the method of Example 1, keeping the reaction at −10° C. and using 1 eq of sodium cyanoborohydride. Yield 42%, $^1$H NMR (400 MHz, CDCl$_3$) δ 8.46 (d, J=4.8 Hz, 1H), 7.44 (d, J=8.4 Hz, 2H), 7.36 (d, J=8.8 Hz, 2H), 7.28-7.24 (m, 2H), 7.08 (d, J=7.5 Hz, 1H), 7.03 (d, J=7.9 Hz, 1H), 6.98 (s, 1H), 5.00 (dd, J=6.2, 10.1 Hz, 1H), 3.36 (dd, J=7.9, 10.6 Hz, 1H), 3.30-3.25 (br s, 1H), 2.84-2.77 (m, 1H), 2.23-2.16 (m, 1H), 1.91-1.82 (m, 1H), 1.47 (s, 3H), 1.42 (s, 3H), 1.18-1.08 (m, 2H), 1.05-0.97 (m, 2H). LC-MS ESI m/z: 565 (M+H)$^+$, T$_r$=2.49 min, method 2.

Example 3

(3R,5R)-3-[1-Methyl-1-(2-trifluoromethyl-pyrimidin-4-yl)-ethylamino]-5-(3-fluoro-phenyl)-1-(4-trifluoromethoxy-phenyl)-pyrrolidin-2-one

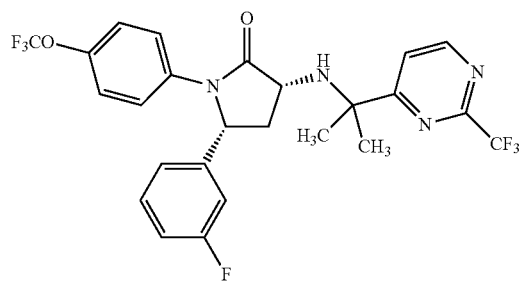 [SMILES: CC(C)(N[C@@H]1C[C@H](c2cccc(F)c2)N(c2ccc(OC(F)(F)F)cc2)C1=O)c1ccnc(C(F)(F)F)n1]

Stir a mixture of 1-(4-trifluoromethoxy-phenyl)-3-(R)-1-phenyl-ethylamino)-5(R)-(3-fluoro-phenyl)-1,5-dihydro-pyrrol-2-one (685 mg, 1.5 mmol), THF (4 mL), water (1 mL), 2,5-dimethoxytetrahyrofuran (0.23 mL, 1.8 mmol), acetic acid (0.34 mL, 6.0 mmol), and trifluoroacetic acid (0.23 mL, 3.0 mmol) at 35° C. for 18 hours. Observe significant formation of (R)-5-(3-fluoro-phenyl)-1-(4-trifluoromethoxy-phenyl)-pyrrolidine-2,3-dione (LC-MS ESI m/z: 354 (M+H)$^+$, T$_r$=2.65 min., method 2). Pour the reaction into saturated aqueous sodium bicarbonate solution and dilute with 10 mL of 1:1 toluene:isopropyl acetate. Separate the organic layer and filter through sodium sulfate. Add acetic acid (0.69 mL, 12.0 mmol) and 1-methyl-1-(2-trifluoromethyl-pyrimidin-4-yl)-ethylamine (339 mg, 1.65 mmol) to this solution containing (R)-5-(3-fluoro-phenyl)-1-(4-trifluoromethoxy-phenyl)-pyrrolidine-2,3-dione. Heat to 55° C. for 24 hours. Concentrate the reaction mixture to give a dark purple oil. Observe significant formation of 3-[1-methyl-1-(2-trifluoromethyl-pyrimidin-4-yl)-ethylamino]-1-(4-trifluoromethoxyphenyl)-5(R)-(3-fluoro-phenyl)-1,5-dihydro-pyrrol-2-one (LC-MS ESI m/z: 541 (M+H)$^+$, T$_r$=3.32 min., method 2). Dissolve the crude 3-[1-methyl-1-(2-trifluoromethyl-pyrimidin-4-yl)-ethylamino]-1-(4-trifluoromethoxyphenyl)-5(R)-(3-fluoro-phenyl)-1,5-dihydro-pyrrol-2-one in acetic acid (6 mL) and THF (1.5 mL), cool to 0° C., and add sodium cyanoborohydride (189 mg, 3.0 mmol). Remove the cooling bath after 5 minutes and stir 30 minutes at ambient temperature. Dilute the reaction with ethyl acetate and slowly pour it into saturated aqueous sodium bicarbonate solution. Concentrate the organic layer under reduced pressure and purify the residue by silica gel chromatography (10-35% ethyl acetate-hexane) to obtain (3R,5R)-3-[1-methyl-1-(2-trifluoromethyl-pyrimidin-4-yl)-ethylamino]-5-(3-fluoro-phenyl)-1-(4-trifluoromethoxy-phenyl)-pyrrolidin-2-one (340 mg, 41%) as a foam. $^1$H NMR (400 MHz, CDCl$_3$): δ 8.79 (d, J=5.3 Hz, 1H), 7.92 (d, J=5.3 Hz, 1H), 7.29-7.26 (m, 2H), 7.22-7.18 (m, 2H), 7.05 (d, J=8.8 Hz, 2H), 6.93 (d, J=7.5 Hz, 1H), 6.90-6.83 (m, 2H), 4.96 (dd, J=6.2, 9.7 Hz, 1H), 3.45

(dd, J=8.1, 10.8 Hz, 1H), 2.84-2.77 (m, 1H), 1.88-1.80 (m, 1H), 1.56 (s, 3H), 1.49 (s, 3H). LC-MS ESI m/z: 543 (M+H)+, T$_r$=2.97 min., method 2.

Example 4

(3R,5R)-3-[1-Methyl-1-(6-trifluoromethyl-pyridin-2-yl)-ethylamino]-5-phenyl-1-(4-trifluoromethoxy-phenyl)-pyrrolidin-2-one

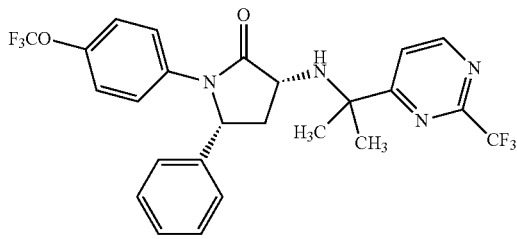 [SMILES: CC(C)(N[C@@H]1C[C@H](c2ccccc2)N(c2ccc(OC(F)(F)F)cc2)C1=O)c1ccnc(C(F)(F)F)n1]

Prepare the title compound essentially as described in the method of Example 3. Yield 47%. $^1$H NMR (400 MHz, CDCl$_3$): δ 8.77 (d, J=5.3 Hz, 1H), 7.93 (d, J=5.3 Hz, 1H), 7.28 (d, J=8.8 Hz, 2H), 7.25-7.17 (m, 2H), 7.16-7.13 (m, 3H), 7.02 (d, J=8.8 Hz, 2H), 4.96 (dd, J=6.2, 9.7 Hz, 1H), 3.46 (dd, J=7.9, 10.6 Hz, 1H), 2.83-2.76 (m, 1H), 1.91-1.83 (m, 1H), 1.56 (s, 3H), 1.49 (s, 3H). LC-MS ESI m/z: 525 (M+H)+, T$_r$=2.92 min, method 2.

Example 5

(3R,5R)-3-[1-Methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one tosylate

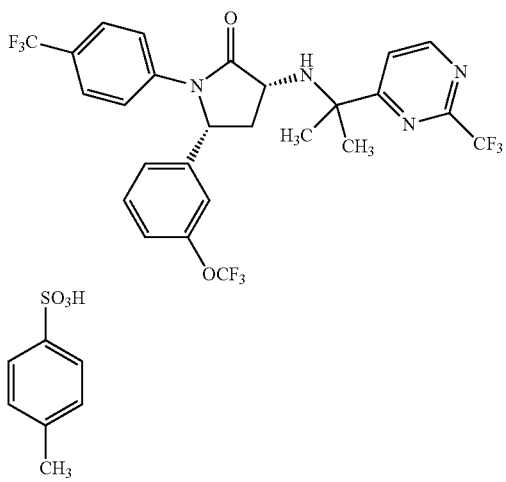

Dissolve (3R,5R)-3-[1-methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one (4.57 g, 7.71 mmol) in isopropanol (10 mL). Add p-toluenesulfonic acid monohydrate (1.49 g, 7.71 mmol) and heat to 45° C. until the solution is homogeneous. Cool to ambient temperature and add seed crystals. Let stand at ambient temperature for 64 hours. Filter the precipitate and wash with heptane. Dry under vacuum for 4 hours to give (3R,5R)-3-[1-methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one tosylate (5.06 g, 86%) as a white powder. LC-MS ESI m/z: 593 (M+H)+, T$_r$=4.92 min., method 1.

Seed Crystal Formation

Dissolve (3R,5R)-3-[1-methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one (61.4 mg, 104 μmol) in isopropanol (1 mL). Add p-toluenesulfonic acid monohydrate (20.0 mg, 104 μmol) to give a homogeneous solution. Add (3R,5R)-3-[1-methyl-1-(6-trifluoromethyl-pyridin-3-yl)-ethylamino]-5-(3-trifluoromethoxy-phenyl)-1-(4-trifluoromethyl-phenyl)-pyrrolidin-2-one tosylate (<1 mg) to initiate crystallization. Expose the solution to the atmosphere and let evaporate to dryness over 18 hours to give (3R,5R)-3-[1-methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one tosylate (77 mg, 97%) as an off white solid.

Example 6

(3R,5R)-3-[1-Methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one adipate

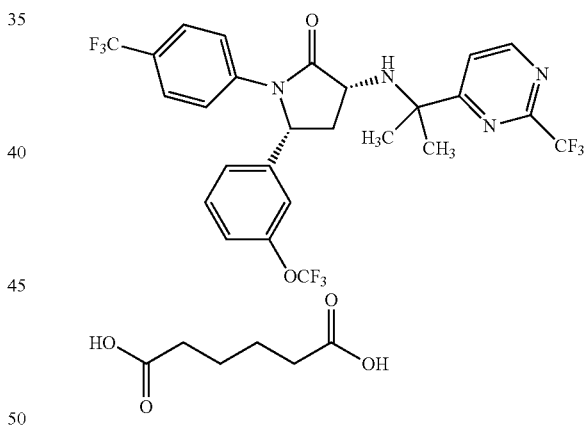

Dissolve (3R,5R)-3-[1-methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one (105 mg, 0.177 mmol) in methanol (0.8 mL) and ethyl acetate (2 mL). Add adipic acid (30 mg, 0.20 mmol) and evaporate at room temperature overnight to give a quantitative mass balance of (3R,5R)-3-[1-methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one adipate (129 mg, 100%) as a candied solid: ES/MS m/z: 593.0 [M+H]+.

As mentioned, the compounds of the present invention are selective and highly potent inverse agonists or antagonists of the CB-1 receptor and are therefore useful in the treatment of various disorders by virtue of this pharmacology. The following assays may be used to demonstrate the claimed compounds' CB-1 receptor activity, their selectivity for the CB-1 receptor, and their activity in animal models of various disorders believed to be treatable by CB-1 receptor inverse agonism or antagonism.

It is noted that by definition, a pure antagonist inhibits the ligand mediated activation of a receptor (i.e. blocks agonist dependent receptor stimulation). Some receptors, including the CB-1 receptor, produce signal transduction even in the absence of agonists (endogenous/exogenous), which is referred to as the receptor's basal activity or consitutive activity. With such receptors, inverse agonists not only inhibit agonist dependent stimulation of the receptor, but also reduce/inhibit the basal activity of the receptor. In that CB-1 receptors have basal signaling activity, inverse agonists are preferred to pure antagonists as therapeutic agents for CB-1 mediated disorders. The compounds of the present invention are selective inverse agonists or antagonists of the CB-1 receptor.

$CB_1$ and $CB_2$ In Vitro Functional Assays

Compounds of the present invention may be tested for functional activity at the CB-1 and CB-2 receptors in both agonist and antagonist modes using SPA (Scintillation Proximity Assay) based GTP-$\gamma$-$^{35}$S binding assays. All assay components are prepared in assay buffer (20 mM HEPES, 100 mM NaCl, 5 mM $MgCl_2$, pH 7.4) at room temperature. Semi-log dilutions of test compound are prepared in assay buffer containing BSA (0.125% final conc.) for the agonist mode assays. For the antagonist mode assays, test compounds are prepared in the same manner but also include an 80% efficacious dose of a full agonist (methanandamide). GTP-$\gamma^{35}$S binding for the antagonist assay may be measured in a 96 well format using a modification of an antibody capture technique previously described. (DeLapp, N W, et al. (1999) *J Pharmacol Exp Ther* 289:946-955.) The CB-2 receptor agonist activity may be measured using a similar method using hCB2-Sf9 membranes. The CB-1 receptor agonist activity may be measured using a whole membrane capture technique using hCB1-CHO membranes. All incubations are done at room temperature.

Antagonist Mode Assays
hCB1-CHO and rCB1-CHO Antagonist Assays:

hCB1-CHO or rCB1-CHO membranes (Applied Cell Sciences, Rockville, Md.) and GDP (1 µM final) are added to ice cold assay buffer and homogenized. Diluted compounds, GTP-$\gamma$-$^{35}$S (500 nM final conc.) and membranes are added to wells of an assay plate and incubated for 30 min. at room temperature. Next, a mixture containing Nonidet P40 detergent (0.2% final conc.), rabbit polyclonal IgG $G\alpha_{i-3}$ antibody (provided by Covance, Princeton, N.J.), and 1.25 mg anti-rabbit antibody scintillation proximity assay beads (GE Healthcare, Piscataway, N.J.) is added. The plates are sealed, vortexed, and incubated for an additional 2 hr. Plates are then centrifuged at 700×g for 10 min. and the radioactivity counted.

hCB1-Sf9 and hCB2-Sf9 antagonist Assays:

hCB1-5f9 and hCB2-5f9 membranes (Perkin Elmer, Boston, Mass.) are prepared essentially as above with 1 µM (final conc.) GDP for hCB1-5f9 and 0.05 µM (final conc.) GDP for hCB2-5f9. The assay is run essentially as described for the CHO membranes above. Diluted membranes are pre-incubated with test compound for 15 min., which is followed by addition of GTP-$\gamma$-$^{35}$S and a further 35 min. incubation. Nonidet P40 and anti-$G_i$-antibody are added sequentially with a 15 min. incubation after each addition. The SPA beads are then added, the plates are sealed and vortexed, and then incubated at room temperature for 1 hr.

Agonist Mode Assays
hCB1-CHO Agonist Assay:

hCB1-CHO membrane, GDP (1 µM final conc.), and saponin (10 ng/mL final conc., Sigma, St Louis, Mo.) are combined and prepared on ice as for the antagonist assays, above. Diluted test compounds, GTP-$\gamma$-$^{35}$S (500 nM final conc.) and membranes are combined in the assay plate and incubated for 30 min. Then 1 mg/well Wheatgerm Agglutinin SPA beads (GE Healthcare, Piscataway, N.J.) are added, plates are sealed and vortexed and incubate for 1 hr. before spinning and counting in the same fashion as for the antagonist assays, above.

hCB2-S19 Agonist Assay:

The hCB2-5f9 assay is run essentially as for the hCB1-sf9 and hCB2-sf9 antagonist assays above, with no challenging agonist added. 1 µM (final conc.) GDP is added to the membrane solution and nonidet P40, anti-$G_i$-antibody, and SPA bead are added together in a cocktail.

Data are analyzed as follows: Background is subtracted from all wells. Percent agonist efficacy is determine by normalizing agonist/inverse agonist dose response data to the response obtained for a full agonist (methanandamide). Percent antagonist inhibition is calculated by first normalizing the data to the signal generated by a saturating concentration of the full agonist (methanandamide). Then the data are analyzed using a 4-parameter logistic reduced fit (Activity Base™ and XLFit3™ from IDBS, Emeryville, Calif.). $K_b$ values are determined using a modification of the Cheng-Prusoff relationship: $K_b$=IC50/(1+[agonist]/EC50), where "IC50" is determined from a four parameter fit of displacement curves, "[agonist]" is the agonist challenge concentration (nM), and "EC50" is determined from a four parameter fit of a full agonist concentration response curve (Cheng and Prusoff 1973). Mean $K_b$ values are calculated as a mean of at least three independent determinations±standard error of the mean (SEM). (Cheng Y C and Prusoff W H. (1973), *Biochem Pharmacol* 22:3099-3108.) Exemplified compounds are found to be potent CB-1 inverse agonists ($K_b \leq 10$ nM, typically <2 nM) and to be selective over the CB-2 receptor ($K_{b\ CB-2}/K_{b\ CB-1}$>500, typically >1000).

Tables 6 and 7 summarize antagonists/inverse agonist properties of certain compounds of the present invention. The data indicate that the test compounds are potent CB-1 inverse agonists at both rat and human receptors and are selective over human CB-2 receptors. The agonist efficacy being less than zero indicates that the compounds decreased basal (constitutive) activity of the CB-1 receptor in vitro, which characterizes the compounds as inverse agonists at the CB-1 receptor.

TABLE 6

| Example No. | rCB-1 SPA GTPγS CHO Membrane Antagonist | hCB-1 SPA GTPγS CHO Membrane Antagonist | hCB-2 SPA GTPγS Sf9 Membrane Antagonist |
|---|---|---|---|
| 1 | 0.177 | 0.895 | >8710 |
| 2 |  | 0.644 | >10800 |
| 3 | 0.195 | 0.916 | 397 |
| 4 | .176 | 0.83 | 288 |

All values are: Kb nM

TABLE 7

| Example No. | hCB-1 SPA GTPγS CHO Membrane Agonist | | hCB-2 SPA GTPγS Sf9 Membrane Agonist Relative $EC_{50}$ (nM) |
|---|---|---|---|
| | Relative $EC_{50}$ inverse (nM) | % Relative Efficacy | |
| 1 | 0..558 | −99.3 | >8710 |
| 2 | 2.39 | −108 | >10800 |
| 3 | 1.11 | −107 | 379 |
| 4 | 2.52 | −105 | 288 |

Force Swim Test (FST)

The forced swim test is a well established animal model for depression, anxiety and avolition (lack of motivation)(Porsolt, et al. *Nature* (1977) 266, 730)(J. M. Witkin et al., *Trends Pharmacol Sci.* 2005 26:609-17). It can also be used as a model for the treatment of negative symptoms of schizophrenia.

Male NIH Swiss mice (Harlan Sprague-Dawley) are housed 12 mice/cage for 7-10 days prior to testing. On the day of testing, mice weighing 25-30 g, are brought to the testing room at least 1 hr. prior to dosing. Mice are dosed (p.o.) at 6-8 min. intervals with either vehicle (1% CMC/0.5% SLS/0.08% povidone/0.05 antifoam for CB1 inverse agonists) or test compound and put it into a clean cage (4 mice/cage).

To test, mice are placed individually in clear plastic cylinders (about 10 cm diameter×25 cm height) filled to 6 cm with water at 22-25° C. for six min. The duration of immobility during the last 4 min. is recorded. A mouse is regarded as immobile when floating motionless or making only those movements necessary to keep its head above the water.

The immobility time (in seconds) is analyzed by ANOVA using Dunnett's test. The minimum effective dose (MED) is considered to be the lowest dose of test compound at which a statistically significant decrease in the immobility time is observed versus the vehicle control.

Bioavailability

Methods for accessing bioavailability are well appreciated in the art. One such reference is *Medicinal Research Reviews* Vol 21 No. 5 382-396 (2001). Bioavailability of compounds may be estimated essentially as follows.

Cohorts of three or four 250-450 gram male Sprague-Dawley rats or approximately 10 kg Beagle dogs (female or male) are used. Animals do not need to be fasted for the i.v. portion of the study. Dogs are administered i.v. by cannulated cephalic vein and blood collections are by jugular vein. Animals are first dosed at 0.25 mg/kg i.v. and blood samples (0.2 mL) are then collected using EDTA as an anticoagulant at 0.0830, 0.25, 0.50, 1, 2, 4, 8, 12, 24, 48, 72, 96, and 120 hours. Next after at least two days and after 18-24 hours fasting, the animals are dosed at 1.0 mg/kg by oral gavage. During the course of a study the total of blood (ml) collected is not to exceed 1% of total body weight in grams. Should larger blood volumes be required, the sampled blood volume is replace with heparinized whole blood from a donor animal. When using a cross-over study design, rats receive a volume of heparinized whole blood following the final sample of each study day approximately equal to that removed during study.

Compound plasma concentrations are measured by LC/MS/MS assays. Data are then analyzed using standard non-compartmental pharmacokinetic analysis. Oral bioavailability is calculated as:

$$(AUC_{0\text{-}infinity}, oral/AUC_{0\text{-}infinity}, i.v.) \times (Dose, i.v./Dose, oral) \times 100\%$$

The compound of Example 5 is tested and found to have rat oral bioavailability as follows:

Fasted, male SD rats
IV: 0.25 mg/kg, formulation: 20% v/v MEOP/80% v/v purified water
PO: 1 mg/kg, formulation: 1% NaCMC/0.5% SLS/0.05% antifoam in purified water
The oral bioavailability is 51+/−19% (mean s.d, n=3 rats) and is based on $AUC_{0\text{-}24hr}$.

Human CYP Fingerprinting

CYP fingerprinting is well established technique and is used as an indication of potential risk of drug-drug interactions in the pharmaceutical sciences. Compounds of the present invention may be assayed by well known methods, essentially as follows: Compounds are incubated at 37° C. at a final concentration of 4 μM with pooled, mixed gender, human liver microsomes and 1 mM NADPH (Nicotine Adenine Dinucleotide Phosphate) (final conc.) for 0 and 30 min. without any CYP inhibitor and with each CYP inhibitor in separate incubations for 30 min. Each inhibitor is specific for an individual cytochrome P450. The specific inhibitors used for CYPs 2C9, 2D6 and 3A were sulfaphenazole, quinidine and ketoconazole, respectively. Ketoconazole (CYP3A) is made up at 25 mM in DMSO and then diluted in buffer to a final concetration of 10 μM. Quinidine (CYP2D6) is made up at 5 mM in 50/50 acetonitrile/water and then diluted in buffer to a final concetration of 10 μM. Sulfaphenazole (CYP2C9) is made up at 100 mM in DMSO and then diluted in buffer to a final concetration of 5 μM. Samples are analyzed by LC-MS in positive or negative electrospray mode using a Waters Acquity Ultra Performance LC coupled to a MicroMass Q-T of-2 mass spectrometer.

Data are analyzed using MetaboLynx™ version 4.1. With inhibitor present, a reduction in metabolite peak area of less than 30% (relative to the uninhibited control incubation) receives a designation of low risk of Drug Drug Interaction (DDI), a reduction in peak area between 30% and 70% receives a moderate risk of DDI and a reduction of more than 70% receives a high risk of DDI.

Exemplified compounds are tested essentially as described and found to have CYP fingerprints as follows:

TABLE 6

Risk of Drug Drug Interaction (DDI)

| Ex No. | CYP3A | CYP2D6 | CYP2C9 |
|---|---|---|---|
| 1 | low | low | low |
| 2 | low | low | low |
| 3 | low | low | low |
| 4 | low | low | low |
| 5 | low | low | |
| 6 | low | low | |

In Vivo Efficacy in Feeding Models

The ability of compounds of the present invention to reduce body weight may be tested in a rat feeding model essentially as follow. Establish diet-induced obese (DIO) male Long-Evans rats by ad lib feeding from weanling on a diet consisting of about 40% fat, about 39% carbohydrate and about 21% protein caloric content for at least 12 weeks.

Administer test compound or vehicle to cohorts of rats (p.o., once daily) for two weeks. Determine compound potency as the dose required to produce a difference of 17 grams compared to the vehicle group after treatment for two weeks (T17 potency). This represents a minimally biologically relevant reduction of 3-4% of body weight compared to vehicle treatment after 2 weeks.

Antipsychotic Weight Gain Model

The ability of compounds of the present invention to maintain/reduce body weight during treatment with antipsychotics may be tested in a rat feeding model essentially as follow. Maintain adult lean, female Sprague-Dawley rats ad libitum on normal rodent chow Purina LabDiet 5001 (12.3% fat) and water. Treat one group (n ~7) with vehicle (1% lactic acid) on days 1-14 while treating the rest with olanzapine (2 mg/kg, po). Follow food intake, monitor body weight and change in fat mass over a two week treatment. After 14 days of drug delivery, divide the olanzapine treated animals (n ~8 per group) and treat one group with 0.3 mg/kg test compound plus olanzapine, treat a second group with 1 mg/kg test compound plus olanzapine and treat the final group with vehicle plus olanzapine for days 15-28.

I claim:

1. A compound of the formula

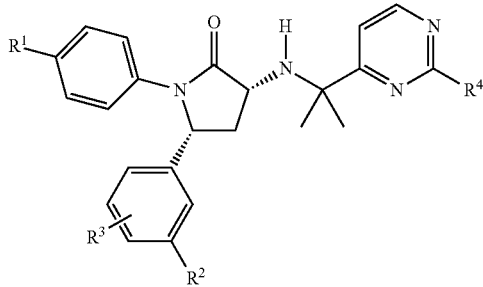

$R^1$ is selected from the group consisting of hydrogen, chloro, cyano, trifluoromethyl, difluoromethoxy, and trifluoromethoxy;

$R^2$ is selected from the group consisting of hydrogen, halo, cyano, ($C_1$-$C_3$) alkyl substituted with from 1 to 5 fluoro groups, and ($C_1$-$C_3$) alkoxy substituted with from 1 to 5 fluoro groups;

$R^3$ is selected from the group consisting of hydrogen, fluoro, and chloro;

$R^4$ is selected from the group consisting of trifluoromethyl, cyano and cyclopropyl;

provided that, when $R^1$ is hydrogen, chloro, cyano, or trifluoromethyl, then $R^2$ is ($C_1$-$C_3$) alkoxy substituted with from 1 to 5 fluoro groups;

or pharmaceutically acceptable salts thereof.

2. The compound according to claim 1 wherein $R^2$ is selected from the group consisting of hydrogen, fluoro, chloro, cyano, trifluoromethyl, 1,1-difluoroethyl, trifluoromethoxy, difluoromethoxy, and 1,1,2,2-tetrafluoroethoxy, or a pharmaceutically acceptable salt thereof.

3. The compound according to claim 2 wherein $R^2$ is selected from the group consisting of trifluoromethyl, 1,1-difluoroethyl, difluoromethoxy, trifluoromethoxy, and 1,1,2,2-tetrafluoroethoxy and $R^3$ is hydrogen, or a pharmaceutically acceptable salt thereof.

4. The compound according to claim 1 wherein $R^1$ is difluoromethoxy or trifluoromethoxy, or a pharmaceutically acceptable salt thereof.

5. The compound according to claim 1 wherein $R^2$ is ($C_1$-$C_3$) alkoxy substituted with from 1 to 5 fluoro groups, or a pharmaceutically acceptable salt thereof.

6. The compound according to claim 5 wherein $R^3$ is hydrogen, or a pharmaceutically acceptable salt thereof.

7. The compound according to claim 1 which is (3R,5R)-3-[1-Methyl-1-(2-trifluoromethyl-pyrimidin-4-yl)-ethylamino]-5-(3-trifluoromethoxy-phenyl)-1-(4-trifluoromethyl-phenyl)-pyrrolidin-2-one, or a pharmaceutically acceptable salt thereof.

8. The compound according to claim 1 which is (3R,5R)-3-[1-(2-Cyclopropyl-pyrimidin-4-yl)-1-methyl-ethylamino]-5-(3-trifluoromethoxy-phenyl)-1-(4-trifluoromethyl-phenyl)-pyrrolidin-2-one, or a pharmaceutically acceptable salt thereof.

9. The compound according to claim 1 which is (3R,5R)-3-[1-Methyl-1-(2-trifluoromethyl-pyrimidin-4-yl)-ethylamino]-5-(3-fluoro-phenyl)-1-(4-trifluoromethoxy-phenyl)-pyrrolidin-2-one, or a pharmaceutically acceptable salt thereof.

10. The compound according to claim 1 which is (3R,5R)-3-[1-Methyl-1-(6-trifluoromethyl-pyridin-2-yl)-ethylamino]-5-phenyl-1-(4-trifluoromethoxy-phenyl)-pyrrolidin-2-one, or a pharmaceutically acceptable salt thereof.

11. A pharmaceutical composition comprising a compound according to claim 1, or a pharmaceutically acceptable salt thereof, and a pharmaceutically acceptable carrier, diluent, or excipient.

12. A method for the treatment of cognitive impairment associated with schizophrenia in a human, comprising administering to a human in need of such treatment, an effective amount of a compound according to claim 1, or a pharmaceutically acceptable salt thereof.

13. A method for the treatment of negative symptoms associated with schizophrenia in a human, comprising administering to a human in need of such treatment, an effective amount of a compound according to claim 1, or a pharmaceutically acceptable salt thereof.

* * * * *